(12) United States Patent  
Schwarz et al.

(10) Patent No.: US 9,299,140 B2
(45) Date of Patent: Mar. 29, 2016

(54) METHOD FOR RECONSTRUCTING CT IMAGE DATA WITH WEIGHTED BACKPROJECTION, INCLUDING COMPUTATION UNIT AND CT SYSTEM FOR THE METHOD

(71) Applicant: SIEMENS AKTIENGESELLSCHAFT, Munich (DE)

(72) Inventors: Karl Schwarz, Roth (DE); Johan Sunnegardh, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 216 days.

(21) Appl. No.: 13/973,031

(22) Filed: Aug. 22, 2013

(65) Prior Publication Data

US 2014/0086466 A1    Mar. 27, 2014

(30) Foreign Application Priority Data

Sep. 24, 2012 (DE) .......................... 10 2012 217 163

(51) Int. Cl.
  *G06K 9/00* (2006.01)
  *G06T 7/00* (2006.01)
  *G06T 11/00* (2006.01)
  *A61B 6/03* (2006.01)
  *A61B 6/00* (2006.01)

(52) U.S. Cl.
  CPC ............ *G06T 7/0012* (2013.01); *G06T 11/006* (2013.01); *A61B 6/032* (2013.01); *A61B 6/5217* (2013.01); *G06T 2211/421* (2013.01)

(58) Field of Classification Search
  CPC .... A61B 6/032; A61B 6/5217; G06T 7/0012; G06T 2211/421; G06T 11/006
  See application file for complete search history.

(56) References Cited

U.S. PATENT DOCUMENTS

| | | | | |
|---|---|---|---|---|
| 6,055,291 A * | 4/2000 | Hu | ................................. | 378/15 |
| 6,459,754 B1 * | 10/2002 | Besson et al. | ..................... | 378/4 |
| 6,522,714 B1 * | 2/2003 | Wang et al. | ..................... | 378/15 |
| 6,678,346 B2 * | 1/2004 | Hsieh | ..................... | G06T 11/005 |
| | | | | 378/4 |

(Continued)

FOREIGN PATENT DOCUMENTS

| | | |
|---|---|---|
| CN | 1489977 A | 4/2004 |
| CN | 1917811 A | 2/2007 |
| CN | 102456227 A | 5/2012 |

OTHER PUBLICATIONS

Sunnegardh J. et al; "Regularized iterative weighted filtered backprojection for helical cone-beam CT", Med. Phys. vol. 35; p. 4173-4185; 2008.

(Continued)

*Primary Examiner* — Gregory M Desire
(74) *Attorney, Agent, or Firm* — Harness, Dickey & Pierce, P.L.C.

(57) ABSTRACT

A method, a computation unit and a CT system are disclosed for reconstructing CT image data, which includes a plurality of image voxels, by way of a weighted filtered back-projection. To weight the projection data during the filtered back-projection, a weight function is used, which weights the projection data from central beams which strike a detector row relatively close to the edge of the row relatively less, and which weights the projection data of central beams, which strike a detector row more relatively centrally, relatively more.

29 Claims, 6 Drawing Sheets

(56) References Cited

U.S. PATENT DOCUMENTS

| | | | |
|---|---|---|---|
| 7,215,734 B2 | 5/2007 | Hsieh et al. | |
| 8,724,889 B2* | 5/2014 | Li et al. | 382/154 |
| 8,923,589 B2* | 12/2014 | Noda | 382/131 |
| 2004/0114707 A1 | 6/2004 | Bruder et al. | |
| 2007/0116177 A1* | 5/2007 | Chen | G01N 23/04 378/57 |
| 2008/0273778 A1* | 11/2008 | Goto et al. | 382/131 |
| 2008/0285708 A1* | 11/2008 | Proksa | A61B 6/032 378/15 |
| 2008/0285709 A1* | 11/2008 | Schwarz | G06T 11/006 378/19 |
| 2009/0207964 A1* | 8/2009 | Pack | A61B 6/032 378/4 |
| 2012/0106832 A1 | 5/2012 | Li et al. | |
| 2012/0170822 A1* | 7/2012 | Litvin | G06T 11/006 382/131 |
| 2013/0101190 A1* | 4/2013 | Shi et al. | 382/131 |
| 2014/0086466 A1* | 3/2014 | Schwarz et al. | 382/131 |

OTHER PUBLICATIONS

Stierstorfer Karl et al., "Weighted FBP—a simple approximate 3D FBP algorithm for multislice spiral CT with good dose usage for arbitrary pitch", in: Phys. Med. Biol., vol. 49, 2004, pp. 2209-2218, DOI: 10.1088/0031-9155/49/11/007.

Image reconstruction an image quality evaluation for a 64-slice CT scanner with z-flying focal spot; T.G. Flohr Image reconstruction an image quality evaluation for a 64-slice CT scanner with z-flying focal spot pp. 2536-2547; Published Medical Physics, vol. 32, No. 8, Aug. 2005; 2005; DE.

Conjugate Cone Beam Backprojection for High Z-resolution Reconstruction; Jiang Hsieh; Conjugate Cone Beam Backprojection for High Z-resolution Reconstruction; pp. 137 bis 141; Published: The Eighth International Meeting on Fully Three-dimensional Image Reconstruction in Radiology and Nuclear Medicine; 2005; DE; Jul. 6, 2005.

German Priority Document German Application 10 2012 217 163.0.
Chinese Office Action and English translation thereof dated Dec. 15, 2016.

* cited by examiner

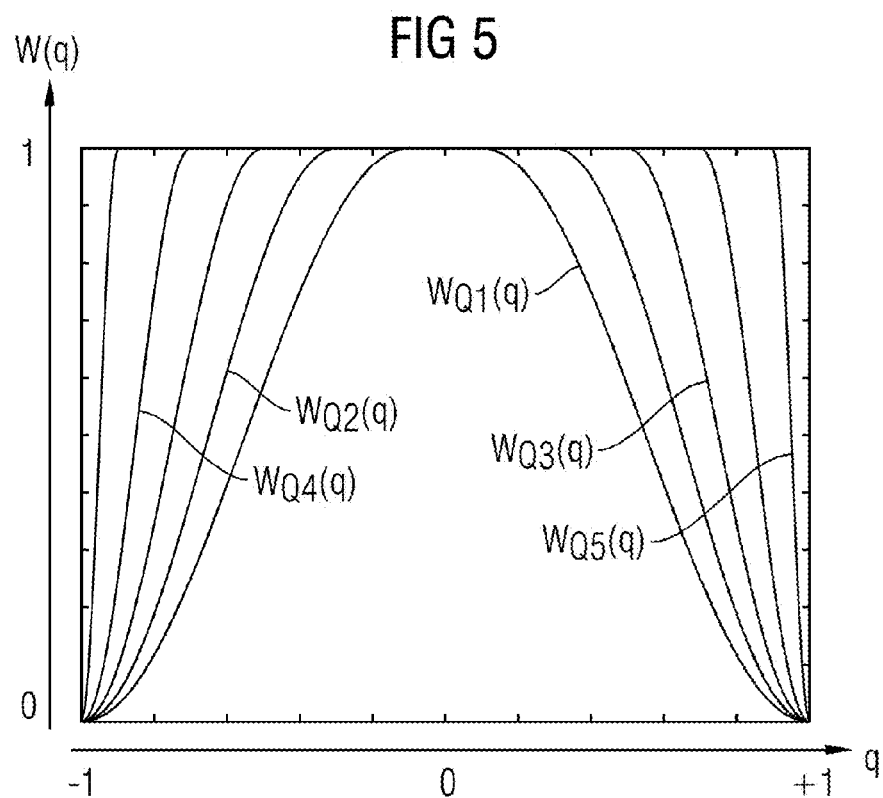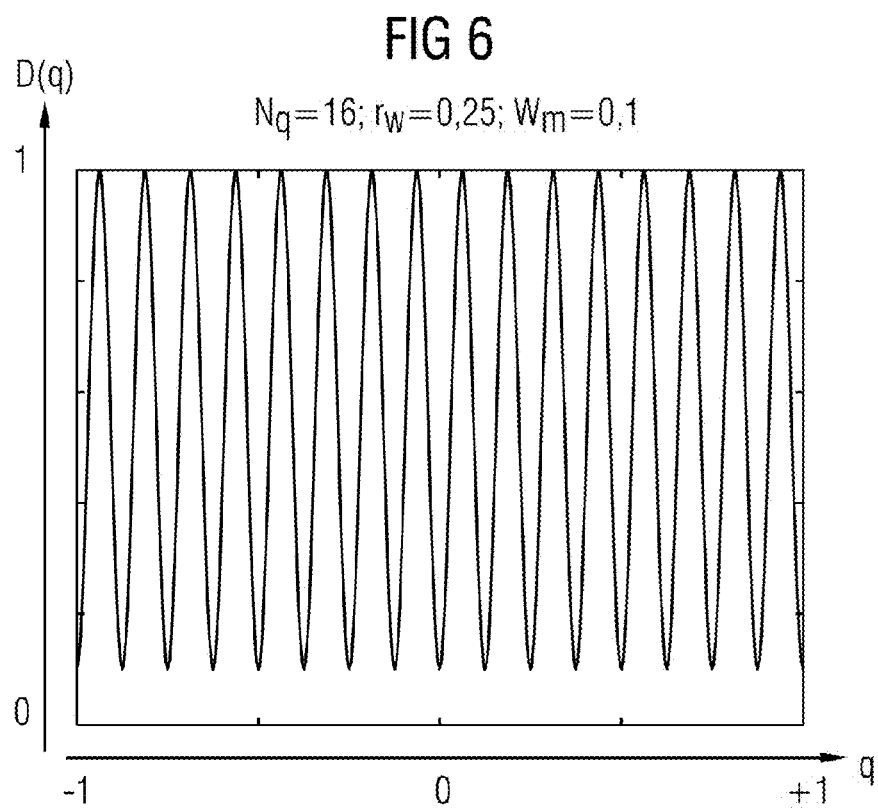

$W(q)D(q)$ $N_q=16; \ Q=0,7; \ r_W=0,25; \ W_m=0,1$ $W(q)D(q)$ $N_q=16; \ Q=0,7; \ r_W=0,1; \ W_m=0,1$

METHOD FOR RECONSTRUCTING CT IMAGE DATA WITH WEIGHTED BACKPROJECTION, INCLUDING COMPUTATION UNIT AND CT SYSTEM FOR THE METHOD

PRIORITY STATEMENT

The present application hereby claims priority under 35 U.S.C. §119 to German patent application number DE 102012217163.0 filed Sep. 24, 2012, the entire contents of which are hereby incorporated herein by reference.

FIELD

At least one embodiment of the invention generally relates to a method for reconstructing CT image data. In at least one embodiment, the method includes a plurality of image voxels, by way of weighted filtered backprojection (WFBP), wherein detector data is received from at least one multirow detector rotating about an examination object, the detector rows of which extend in a peripheral direction perpendicular to a system axis of a CT system, projection data from the detector data of adjacent beams is interpolated, wherein one projection data item of a central beam through the image voxel for each predefined projection angle corresponds to each image voxel and wherein a detector row coordinate relative to the detector is allocated to each projection data item, which corresponds to the position of the central beam on the detector, and a weighting of the projection data is performed as a function of the detector row coordinate allocated to each projection data item. At least one embodiment of the invention also generally relates to a computation unit and/or a CT system for performing said reconstruction method.

BACKGROUND

A reconstruction method is generally known as WFBP reconstruction. Reference is made by way of example in this regard to the publication by Stierstorfer et al., Phys. Med. Biol. 49 pp. 2209-2218, 2004, in which such a reconstruction by weighted filtered backprojection is disclosed.

Such a WFBP method is usually made up of four steps, with a conversion from cone beam detector data to parallel data generally being used for practical reasons, to facilitate the actual reconstruction from a computation point of view.

In the first step raw detector data is measured with a CT system, with the discrete coordinates used here being related as follows to the continuous coordinates:

$\beta = \beta_0 + k_\beta \Delta\beta$, $q = q_0 + k_q \Delta q$, $\alpha = \alpha_0 + k_\alpha \Delta\alpha$, where β describes the fan angle of the measurement beam, q the detector channel and α the angular position of the focus, and $\beta_0$, $q_0$, $\alpha_0$ respectively describe the start of measurement and $\Delta\beta$, $\Delta q$, $\Delta\alpha$ respectively describe the increments of the measurement steps.

In the second step of the WFBP method the existing cone beam detector data $P_{raw}[k_\beta, k_q, k_\alpha]$ rebinned to rebinned parallel projection data $P_{raw}[k_p, k_q, k_\theta]$. A transition is made here from discrete cone beam coordinates β, q, α to discrete parallel beam coordinates p, q, θ, with p representing the channel index, q the detector row coordinate and θ the parallel projection angle.

In the third step the rebinned parallel projection data $P_{reb}[k_p, k_q, k_\theta]$ is convolved with a ramp filter to produce the convolved projection data $P_{conv}(p, q, \theta)$, the geometry of the data not changing here.

In the fourth and last step the convolved projection data is backprojected onto the volume to be reconstructed. This is described mathematically by the formula $$V_{x,y,z} = \sum_\theta \frac{1}{\sum_k W(q)} \sum_k W(q) \cdot P_{conv}(p, q, \theta + k\pi)$$

where $V_{x,y,z}$ corresponds to the value of the reconstructed image voxel at the Cartesian coordinates x, y and z of a CT representation, $P_{conv}(p, q, \theta+k\pi)$ represents the convolved and rebinned projection data in parallel coordinates, where k is a whole number, which represents the number of half rotations of the detector during scanning, the detector row coordinate q describes a central beam of the image voxel $V_{x,y,z}$ projected onto the detector at point x, y, z in the system axis direction with values between −1 and +1 standardized over the detector width and W(q) represents a detector row coordinate-dependent weighting function, which weights rows at the edges of the detector in a decreasing manner toward the edge for artifact reduction.

In principle such a method gives rise to the problem that a projection of an image voxel onto a scanning detector only seldom strikes the center of a detector row. It is therefore necessary to calculate the projection data used to perform the WFBP reconstruction initially from adjacent detector data, in some instances after prior rebinning to parallel data, by way of interpolation. In one particularly simple variant only detector data from directly adjacent detector rows is used.

This has the disadvantage that the spatial resolution of the resulting images in the z direction deteriorates due to the interpolation of the projection data from detector data.

SUMMARY

At least one embodiment of the invention is directed to improving the spatial resolution of the projection data, which has deteriorated due to interpolation of the detector data, and therefore to improve the image data reconstructed therefrom.

Advantageous developments of the invention are set out in the subordinate claims.

The inventors have identified that it is possible to improve the resolution of the reconstructed image data by subjecting the projection data used for WFBP reconstruction, to which relative detector row coordinates are assigned, to a weighting, which weights the projection data, the detector coordinates of which are closer to the center of a detector row, more than projection data, the detector coordinates of which are further away from the center of a detector row.

This results in a detector row coordinate-dependent weighting function, which alternates over the detector rows and thereby weights projection data, the detector row coordinates of which are close to the row center, more and projection data, the detector row coordinates of which are further away from the row center, less. This weighting function can preferably also be overlaid with the weighting function known per se, which weights detector rows close to the edge in the z direction less than centrally located detector rows, so that the detector rows close to the edge tend to be weighted less while a maximum weighting is present at the row center within the row width. The known weighting function is thus overlaid by a weighting that alternates with row width.

One important advantage of an embodiment of this inventive procedure is that already existing backprojectors implemented as hardware can be used without modification for the FBP reconstruction, as only the projection data supplied there has to be subjected to an inventive weighting.

Therefore the inventors propose a method for improving the reconstruction of CT image data, wherein the CT image data includes a plurality of image voxels and the reconstruction is performed by way of a weighted filtered backprojection (WFBP), comprising the following:

receiving detector data, from at least one multirow detector rotating about an examination object, the detector rows of which extend in a peripheral direction perpendicular to a system axis of a CT system, calculation of convolved projection data from the detector data of adjacent beams, wherein one projection data item of a central beam through the image voxel for each predefined projection angle corresponds to each image voxel and wherein a detector row coordinate relative to the detector is allocated to each projection data item, which corresponds to the position of the central beam on the detector, weighting the projection data as a function of the detector row coordinate allocated to each projection data item.

An embodiment of the inventive method can be applied particularly advantageously to detector data that originates from a CT spiral scan, in particular when an advance speed is used, which produces overlapping scan regions.

Alternatively however it is also possible to perform the inventive method in the context of detector data that originates from a CT circular scan. The circular scan can also cover more than 360° or be performed with a number of overlapping scan regions.

It should also be noted that an embodiment of the inventive method can also be used in conjunction with an iterative reconstruction method.

The inventors therefore also propose a method for the iterative reconstruction of CT image data, which includes a plurality of image voxels, wherein:

at least one weighted backprojection of convolved projection data is performed in the iteration, the convolved projection data is calculated from the detector data of adjacent beams, and one projection data item of a central beam through the image voxel for every predefined projection angle is assigned to each voxel, and a detector row coordinate relative to the detector, which corresponds to the position of the central beam on the detector, is allocated to each projection data item.

In addition to an embodiment of the inventive method, the scope of the invention also covers a computation unit for performing a WFBP reconstruction, having at least one processor, a memory for computer programs and an output unit, with a computer program being stored in the program memory, which performs the method steps of one of the inventive methods.

The computation unit can also have at least one manually operable controller, by which at least one parameter can be set before each image calculation, defining the form of at least one weighting function. This allows the user of the system to perform multiple image calculations with individually selected parameters, thereby achieving an optimum compromise between dose utilization and width of the projection data used by way of visual consideration of the image results achieved.

An embodiment of the invention also includes a CT system with a computation unit as described above.

BRIEF DESCRIPTION OF THE DRAWINGS

Embodiments of the invention are described in more detail below with the aid of the figures, in which only the features required for an understanding of the invention are illustrated. The following reference characters and variables are used: 1: CT system; 2: first x-ray tube; 2.1: focus; 3: first multirow detector; 4: second x-ray tube; 5: second multirow detector; 6: gantry housing; 6.1: gantry; 7: patient; 8: patient couch; 9: system axis; 10: computation unit; q: detector row coordinate; M: center lines; Prg1-Prgn: computer programs; S: beam bundle; W(q): first weight function; D(q): second weight function; $\tilde{W}$(q): new weight function; WQ1($q$)-WQ4($q$): profiles of first weighting function.

In the drawings:

FIG. 5: shows an exemplary profile of the first weighting function W(q) over the rows of a multirow detector with reduced weight for rows at the edge;

FIG. 6: shows an exemplary profile of the second weighting function D(q) over the rows of a multirow detector with alternating weighting over the rows with maximum at the row center line and minimum at the edge of the row;

DETAILED DESCRIPTION OF THE EXAMPLE EMBODIMENTS

Figure 1:
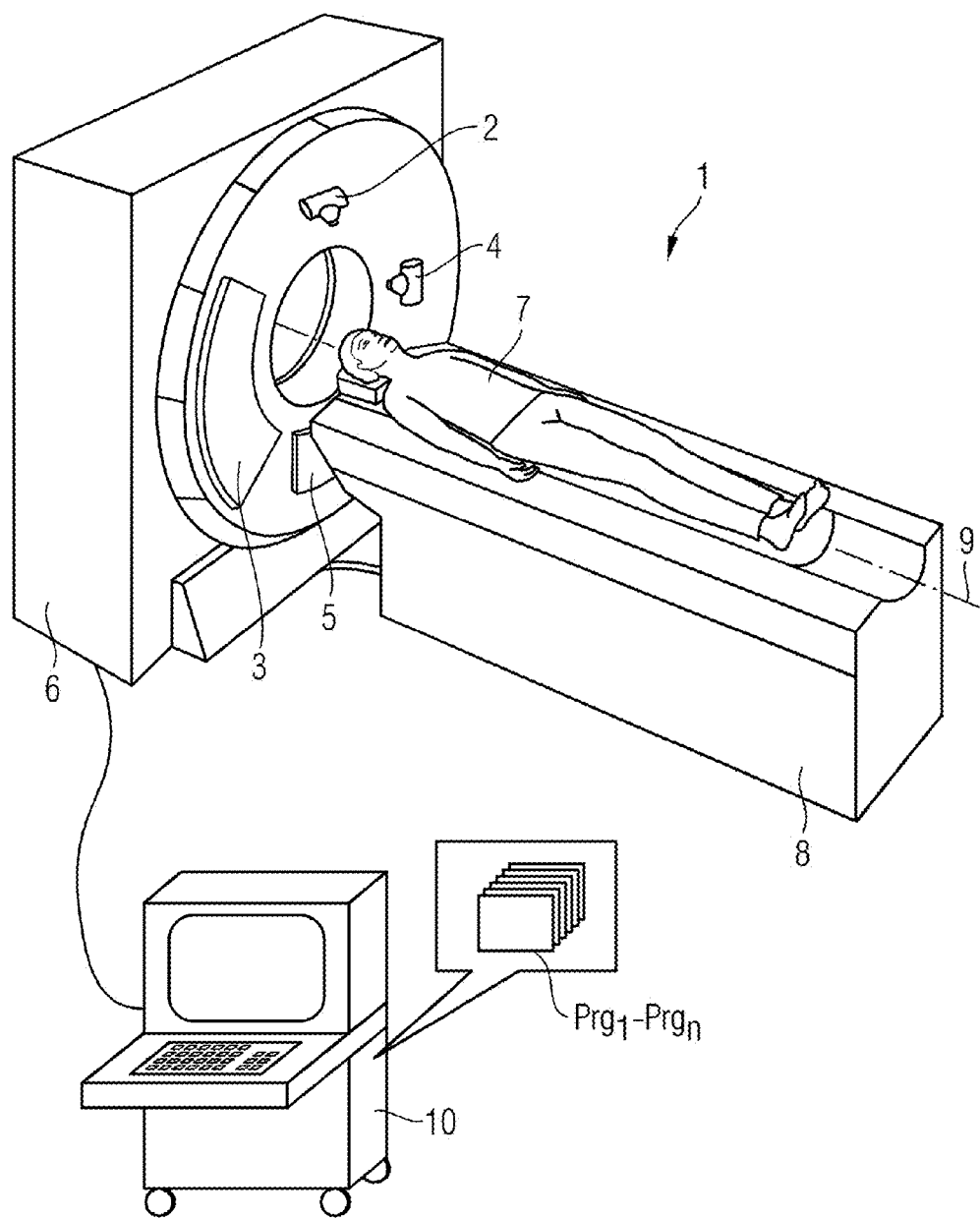
FIG. 1: shows a CT system with computation unit for performing an embodiment of the inventive method.

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

At least one embodiment of the invention is directed to improving the spatial resolution of the projection data, which has deteriorated due to interpolation of the detector data, and therefore to improve the image data reconstructed therefrom.

Advantageous developments of the invention are set out in the subordinate claims.

The inventors have identified that it is possible to improve the resolution of the reconstructed image data by subjecting the projection data used for WFBP reconstruction, to which relative detector row coordinates are assigned, to a weighting, which weights the projection data, the detector coordinates of which are closer to the center of a detector row, more than projection data, the detector coordinates of which are further away from the center of a detector row.

This results in a detector row coordinate-dependent weighting function, which alternates over the detector rows and thereby weights projection data, the detector row coordinates of which are close to the row center, more and projection data, the detector row coordinates of which are further away from the row center, less. This weighting function can preferably also be overlaid with the weighting function known per se, which weights detector rows close to the edge in the z direction less than centrally located detector rows, so that the detector rows close to the edge tend to be weighted less while a maximum weighting is present at the row center within the row width. The known weighting function is thus overlaid by a weighting that alternates with row width.

One important advantage of an embodiment of this inventive procedure is that already existing backprojectors implemented as hardware can be used without modification for the FBP reconstruction, as only the projection data supplied there has to be subjected to an inventive weighting.

Therefore the inventors propose a method for improving the reconstruction of CT image data, wherein the CT image data includes a plurality of image voxels and the reconstruction is performed by way of a weighted filtered backprojection (WFBP), comprising the following:

receiving detector data, from at least one multirow detector rotating about an examination object, the detector rows of which extend in a peripheral direction perpendicular to a system axis of a CT system, calculation of convolved projection data from the detector data of adjacent beams, wherein one projection data item of a central beam through the image voxel for each predefined projection angle corresponds to each image voxel and wherein a detector row coordinate relative to the detector is allocated to each projection data item, which corresponds to the position of the central beam on the detector, weighting the projection data as a function of the detector row coordinate allocated to each projection data item.

For the determination of the relative detector row coordinate reference is made by way of example to the publication already cited above by Stierstorfer et al., Phys. Med. Biol. 49 pp. 2209-2218, 2004, where the calculation of the relative detector row coordinates used here is described in equations (7) and (14).

An embodiment of an inventive improvement of this reconstruction method includes using a weight function to weight the projection data during the filtered backprojection, which weights the projection data of central beams, which strike a detector row close to the edge of the row, less and weights the projection data of central beams, which strike a detector row more centrally, more.

This means that projection data, which strikes the center of a detector row more efficiently, is specifically valued higher than projection data, the detector row coordinate of which is between two detector rows. Position-dependent weighting of the projection data therefore takes place, with distances in the region of a detector row width resulting in significant variations in respect of the weighting used.

While the method just described is essentially directed toward improving an FBP reconstruction, in one particularly preferred variant the WFBP reconstruction method can also be improved by embodying the weighting function additionally so that the weighting of the projection data by the weight function, when considered from row to row, weights projection data with detector row coordinates close to the detector edge generally less and projection data with detector row coordinates in the center of the detector more.

Although an embodiment of the proposed inventive method functions using a cone beam reconstruction, it is however primarily proposed that rebinning be performed before the WFBP reconstruction, after which all the projections used are present in parallel beam geometry, making the actual reconstruction according to the FBP method easier to perform.

One advantage of this inventive technique compared with the known application of an interpolation of conjugate beam pairs is that information not only relating to two adjacent beams but also to any number of beams close to the voxel in question is used automatically. This means that redundant information is not only used to improve resolution but also to improve the signal to noise ratio.

The following formula can specifically be used to reconstruct the image voxels according to the WFBP method:

$$V_{x,y,z} = \sum_\theta \frac{1}{\sum_k \tilde{W}(q)} \sum_k \tilde{W}(q) \cdot P_{conv}(p, q, \theta + k\pi),$$

where:
- $V_{x,y,z}$ corresponds to the value of the reconstructed voxel at the Cartesian coordinates x, y and z,
- $P_{conv}(p, q, \theta+k\pi)$ corresponds to the rebinned and convolved projection data,
- θ corresponds to the parallel projection angle between 0 and 180°,
- k corresponds to a whole number, which represents the number of half rotations of the detector during scanning,
- q corresponds to the detector row coordinate of the central beam of the voxel $V_{x,y,z}$ projected onto the detector at point x,y,z in the system axis direction with values between −1 and +1 standardized over the detector width, and
- $\tilde{W}(q)$ corresponds to the detector row coordinate-dependent weighting function in the WFBP reconstruction.

The inventors also propose, in at least one embodiment, that the WFBP reconstruction method which is known per se and in which a weighting takes place across the detector rows which weights the edge rows less than centrally located rows is modified in such a manner that to weight the projection data during the filtered back-projection a weight function is used, which is a product of a first weighting function and a second weighting function, wherein:

the first weighting function weights projection data of detector rows located close to the edge in the system axis direction in the detector increasingly less toward the edge than projection data of inner detector rows, and the second weight function has a value profile that alternates multiple times over the detector rows in the system axis direction.

This allows very simple implementation of the method on existing CT systems, which already perform a WFBP method and to this end have an WFBP projector, preferably implemented as hardware, as only the inventive minor row weighting, in other words the comb-type weighting over the rows, has to be overlaid with the already existing cross-detector weighting with a weight reduction at the detector edge.

It is particularly advantageous here if the alternating value profile of the second weight function has a maximum in each instance in the center of the detector rows, it being possible for the maximum to form a plateau, and/or for the alternating value profile of the second weight function to have a minimum in each instance between the detector rows. For example a sine function can thus be used for the second weighting function, its maxima and minima being synchronized respectively with the row center and the edge of the row.

The overlaying of the weight function here can be calculated according to the formula $\tilde{W}(q)=W(q)\cdot D(q)$, where:
- $\tilde{W}(q)$=new weight function,
- W(q)=first weight function,
- D(q)=second weight function,
- q coordinate of the detector row in the system axis direction.

The first weight function can also have a value profile, for which the following applies:

$W(q) = 1$ for $|q| < Q$, $W(q) = \cos^2\left(\frac{|q|-Q}{Q-1} \cdot \frac{\pi}{2}\right)$ for $Q \leq |q| < 1$, $W(q)=0$ for all other values of q, where q is a coordinate of the detector row in the system axis direction and Q is a predefined constant value between 0 and 1, which determines the plateau width of the weight function.

An example calculation of the value profile of the second weight function can take place using the following formula:

$$D(q) = \begin{cases} \frac{1+W_m}{2} + \frac{1-W_m}{2}\cos\left(\frac{r}{r_w}\pi\right), & \text{for } r \leq r_w \\ \frac{1+W_m}{2} + \frac{1-W_m}{2}\cos\left(\frac{r-r_w}{1-2r_w}\pi + \frac{\pi}{2}\right), & \text{for } r_w < r \leq 1-r_w \\ \frac{1+W_m}{2} + \frac{1-W_m}{2}\cos\left(\frac{r-(1-r_w)}{r_w}\frac{\pi}{2} + \frac{3\pi}{2}\right), & \text{for } r \geq 1-r_w \end{cases}$$

with:

$$r = \frac{q+1}{2}N_q - 0.5 - \left[\frac{q+1}{2}N_q - 0.5\right]$$

where:
$N_q$ corresponds to the number of detector rows in the detector used,
the parameter $W_m$ can have values between 0 and 1, corresponding to the minimum values for D(q), and
the parameter $r_w$ for defining the peak width can have values between 0 and 0.5.

By varying the constant $r_w$ it is therefore possible for example to calculate different image data with peak widths of different sizes from previously determined detector data. Better dose utilization takes place at a greater peak width and a spatially more precise selection of the significantly weighted projection data takes place with a smaller peak width.

To reconstruct the voxels according to the WFBP method it is further proposed that the following formula be used:

$$V_{x,y,z} = \sum_{\theta} \frac{1}{\sum_k W(q) \cdot D(q)} \sum_k W(q) \cdot D(q) \cdot P_{conv}(p, q, \theta + k\pi),$$

where:

$V_{x,y,z}$ corresponds to the value of the reconstructed voxel at the Cartesian coordinates x, y and z, $P_{conv}(p, q, \theta+k\pi)$ corresponds to the rebinned and convolved projection data, $\theta$ corresponds to the parallel projection angle between 0 and 180°, k corresponds to a whole number, which represents the number of half rotations of the detector during scanning, q corresponds to the detector row coordinate of the voxel $V_{x,y,z}$ projected onto the detector at point x,y,z in the system axis direction with values between −1 and +1 standardized over the detector width, W(q) corresponds to the first weighting function and D(q) corresponds to the second weighting function.

The weighting for the WFBP reconstruction can also be performed here for every projection independently of other projections from further circuits of the detector.

An embodiment of the inventive method can be applied particularly advantageously to detector data that originates from a CT spiral scan, in particular when an advance speed is used, which produces overlapping scan regions.

Alternatively however it is also possible to perform the inventive method in the context of detector data that originates from a CT circular scan. The circular scan can also cover more than 360° or be performed with a number of overlapping scan regions.

It should also be noted that an embodiment of the inventive method can also be used in conjunction with an iterative reconstruction method.

The inventors therefore also propose a method for the iterative reconstruction of CT image data, which includes a plurality of image voxels, wherein:

at least one weighted backprojection of convolved projection data is performed in the iteration, the convolved projection data is calculated from the detector data of adjacent beams, and one projection data item of a central beam through the image voxel for every predefined projection angle is assigned to each voxel, and a detector row coordinate relative to the detector, which corresponds to the position of the central beam on the detector, is allocated to each projection data item.

The inventive improvement of an embodiment of the method is achieved in that to weight the projection data a weight function is used, which weights the projection data of central beams, which strike a detector row close to the edge of the row, less and weights the projection data of central beams, which strike a detector row more centrally, more.

The weighting of the projection data by the weight function can advantageously be performed in such a manner that, when considered from row to row, projection data with detector row coordinates close to the detector edge are generally weighted less and projection data with detector row coordinates in the center of the detector are weighted more.

It is further proposed that:

to weight the convolved projection data a weight function is used, which is a product of a first weighting function and a second weighting function, wherein:

the first weight function weights projection data of detector rows located close to the edge in the system axis direction in the detector increasingly less toward the edge than projection data of inner detector rows, and the second weight function has a value profile that alternates multiple times over the detector rows in the system axis direction.

In respect of the embodiment of the alternating value profile of the second weight function it is proposed that it has a maximum in each instance in the center of the detector rows or alternatively that the alternating value profile of the second weight function has greater values in each instance in the center of the detector rows than toward the edge of the detector rows.

In addition to an embodiment of the inventive method, the scope of the invention also covers a computation unit for performing a WFBP reconstruction, having at least one processor, a memory for computer programs and an output unit, with a computer program being stored in the program memory, which performs the method steps of one of the inventive methods.

The computation unit can also have at least one manually operable controller, by which at least one parameter can be set before each image calculation, defining the form of at least one weighting function. This allows the user of the system to perform multiple image calculations with individually selected parameters, thereby achieving an optimum compromise between dose utilization and width of the projection data used by way of visual consideration of the image results achieved.

An embodiment of the invention also includes a CT system with a computation unit as described above.

To explain embodiments of the invention in more detail, FIG. 1 shows a CT system 1 with a gantry housing 6, in which a multirow detector 3 with an opposing x-ray tube 2 is present on a gantry. From the x-ray tube 2 or more specifically the focus generated there a beam bundle is directed onto the opposing detector during a rotation of the gantry and the patient 7 is moved with the aid of the patient couch 8 sequentially or preferably continuously for a spiral scan in the direction of the system axis 9 through the measurement field in the beam bundle and the attenuation of the beams is measured. Optionally a second beam bundle can also be used at the same time for scanning, being directed from a second x-ray tube 4 onto a second multirow detector 5 disposed with an angle offset on the gantry. If the same x-ray spectra are used in both tube detector systems, the determined detector data can be used together to reconstruct image data.

The CT system 1 is controlled by a computation unit 10, in which computer programs Prg1-Prgn are stored, which during operation also perform inter alia the inventive reconstruction method.

Figure 2:
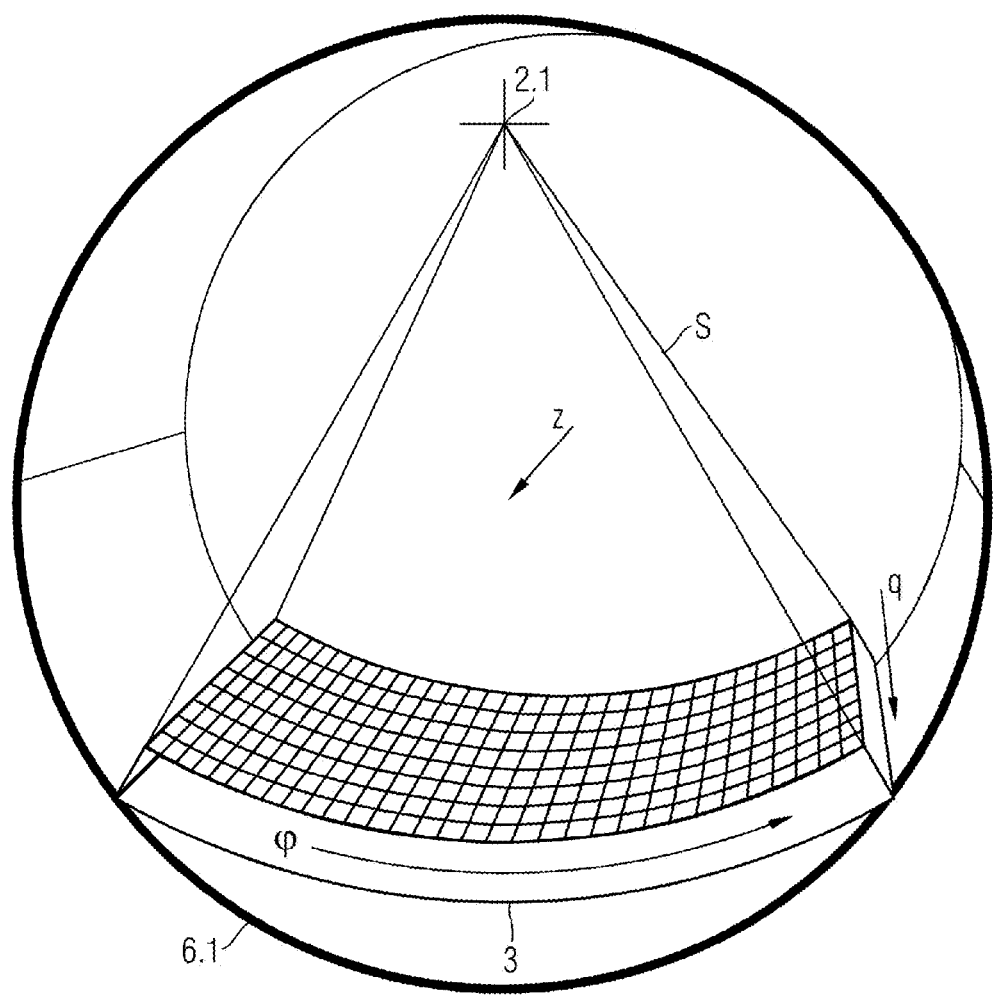
FIG. 2: shows a schematic diagram of a multirow detector in a gantry.

FIG. 2 shows a schematic 3D section from the CT system with a gantry 6.1, which is disposed in the previously illustrated gantry housing. It shows the emitter/detector system with the focus 2.1 disposed in the x-ray tube, from which the beam bundle S is directed onto a multirow detector 3 with detector rows, which extend along the peripheral direction according to the marked φ coordinate. The positions of the detector rows are determined here by a detector row coordinate q, which is generally aligned parallel to the system axis of the CT system. The system axis corresponds—when the gantry is not tilted—to the similarly marked z axis of the Cartesian coordinates system of the CT system.

Figure 3:
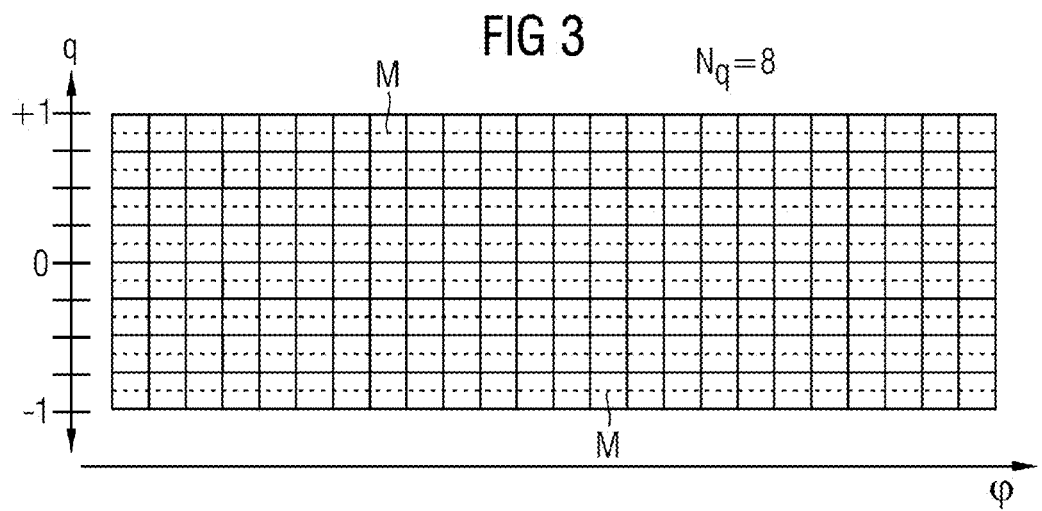
FIG. 3: shows a plan view of an 8-row detector.

Looking at the multirow detector 3 from FIGS. 1 and 2 in a planar diagram looking down on the focus gives the diagram in FIG. 3. The exemplary multirow detector 3 is shown here with Nq=8 detector rows and 24 detector channels. Marked on the detector rows, which extend along the φ axis, with a broken row are their center lines M. The detector row coordinates q, which are preferably standardized over the detector width, are also shown with values between −1 and +1. The center lines M therefore have the detector row coordinates $q \in \{-1+1/N_q, -1+3/N_q, -1+5/N_q, \ldots, 1-1/N_q\}$ while the boundaries between the detector rows have the detector row coordinates $q \in \{-1, -1+2/N_q, -1+4/N_q, \ldots, 1\}$.

Figure 4:
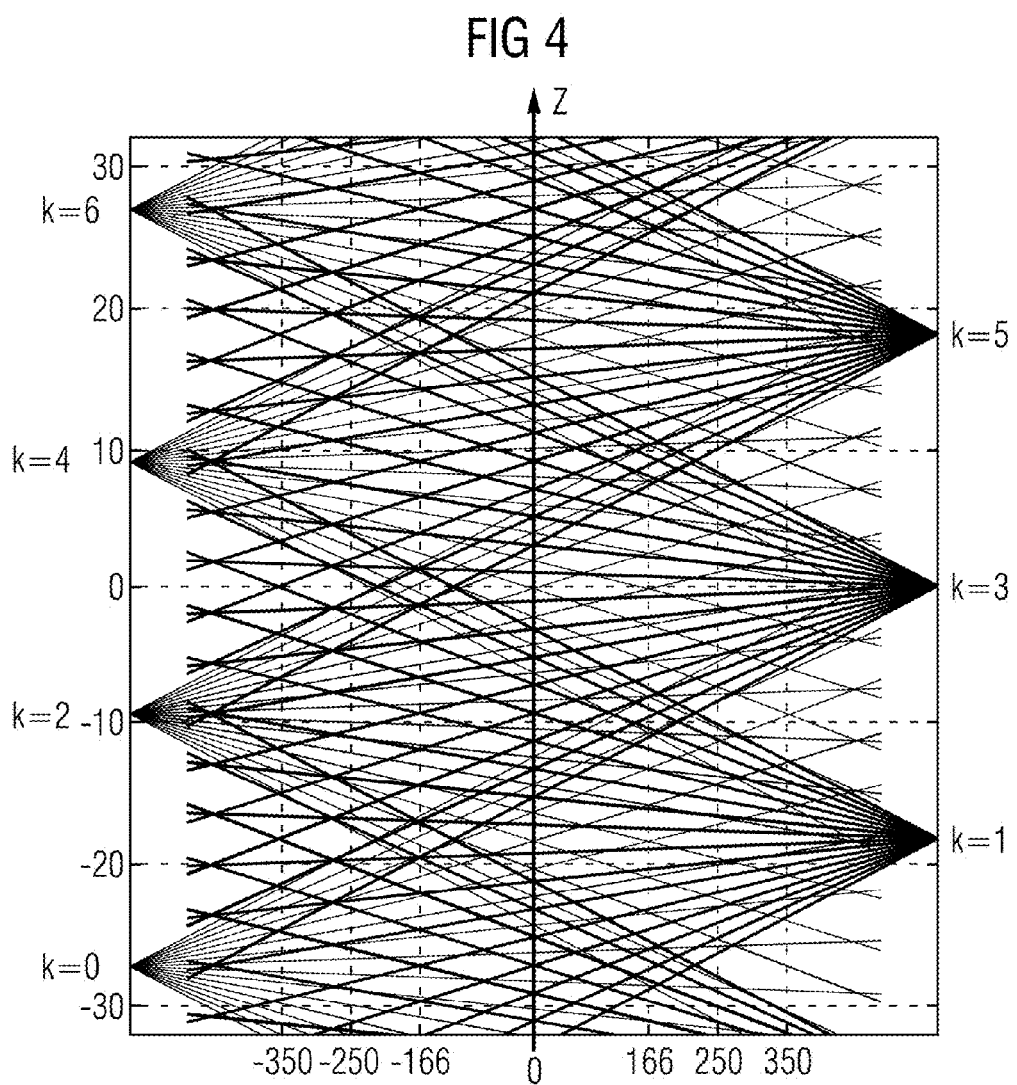
FIG. 4: shows a schematic diagram of the beams of projections in each instance at half rotation positions of detector and focus at k positions.

Looking at a section along the z axis when a multirow detector performs a spiral scan gives the image shown in FIG. 4 of the beams between the focus at positions k and the opposing detector.

The relative detector row coordinates are calculated as illustrated by way of example in the already cited publication by Stierstorfer et al., Phys. Med. Biol. 49 pp. 2209-2218, 2004. The equations (7) and (14) are given there for the calculation of the relative detector row coordinates used here.

To describe the invention based on an already existing first weighting function with reduced weighting of the detector rows close to the detector edge, a first weighting function W(q) can be used, as shown for example in FIG. 5. This Figure shows the profile of the first weighting function W(q) for which the following applies:

$$W(q) = 1 \text{ for } |q| < Q,$$

$$W(q) = \cos^2\left(\frac{|q|-Q}{Q-1} \cdot \frac{\pi}{2}\right) \text{ for } Q \leq |q| < 1,$$

W(q)=0 for all other values of q, where q is a coordinate of the detector row in the system axis direction and Q is a predefined constant value between 0 and 1, which determines the plateau width of the weight function.

Five profiles $WQ1(q)$ to $WQ5(q)$ are shown with different values for the parameter Q.

According to an embodiment of the invention this first weighting function can be overlaid with a second weighting function, which ensures that from the total sum of the existing projection data the projection data weighted in the FBP reconstruction is the projection data which has an optimum spatial correspondence with the theoretical central beams, as determined by the image voxel to be reconstructed. This produces a weighting function over the detector row coordinates of the determined projection data, which in an alternating manner has a maximum at and close to the center line of the detector rows and a minimum at the transition from detector row to detector row. FIG. 6 shows an example of a profile of such a second weighting function D(q) with relatively large peak width.

The second weight function D(q) here follows a value profile, for which the following applies:

$$D(q) = \begin{cases} \frac{1+W_m}{2} + \frac{1-W_m}{2}\cos\left(\frac{r}{r_w}\frac{\pi}{2}\right), & \text{for } r \leq r_w \\ \frac{1+W_m}{2} + \frac{1-W_m}{2}\cos\left(\frac{r-r_w}{1-2r_w}\pi + \frac{\pi}{2}\right), & \text{for } r_w < r \leq 1-r_w \\ \frac{1+W_m}{2} + \frac{1-W_m}{2}\cos\left(\frac{r-(1-r_w)}{r_w}\frac{\pi}{2} + \frac{3\pi}{2}\right), & \text{for } r \geq 1-r_w \end{cases}$$

with:

$$r = \frac{q+1}{2}N_q - 0.5 - \left[\frac{q+1}{2}N_q - 0.5\right]$$

where:

$N_q$ corresponds to the number of detector rows in the detector used, the parameter $W_m$ can have values between 0 and 1, corresponding to the minimum values for D(q), and the parameter c to define the peak width can have values between 0 and 0.5.

In the specifically illustrated instance in FIG. 6 the parameters rw=0.25 and Wm=0.1 have been selected, with a 16-row multirow detector being assumed with Nq=16.

Figure 7:
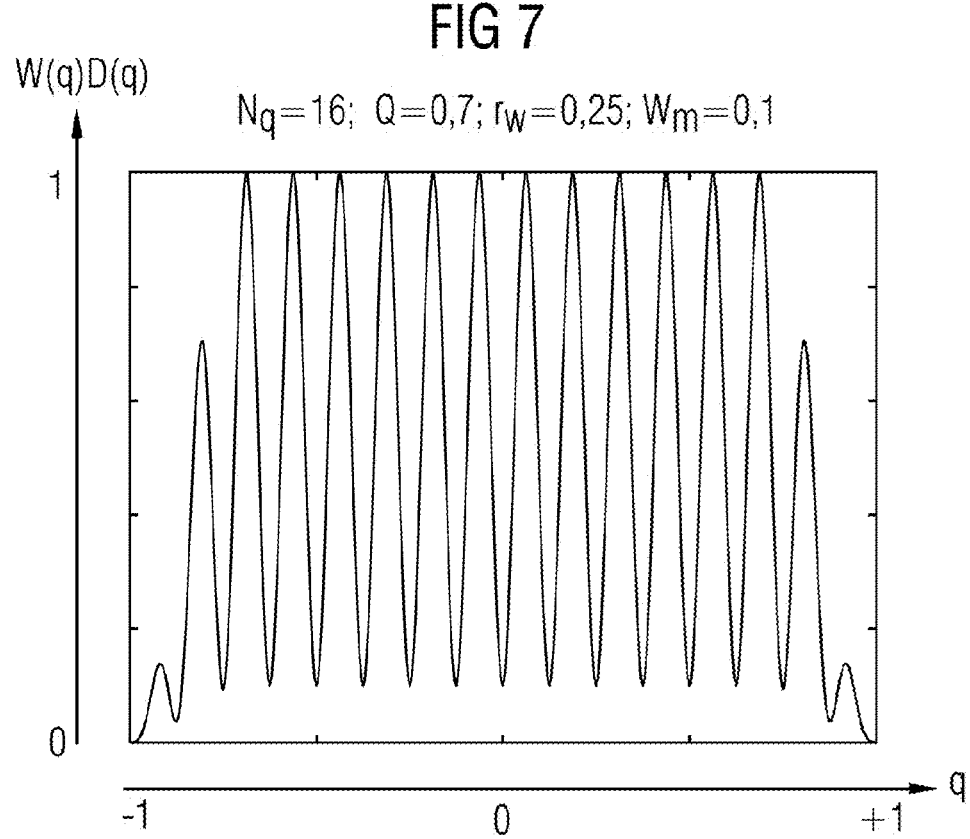
FIG. 7: shows the overlaying of the first and second weight functions from FIGS. 5 and 6 by product formation.
Figure 8:
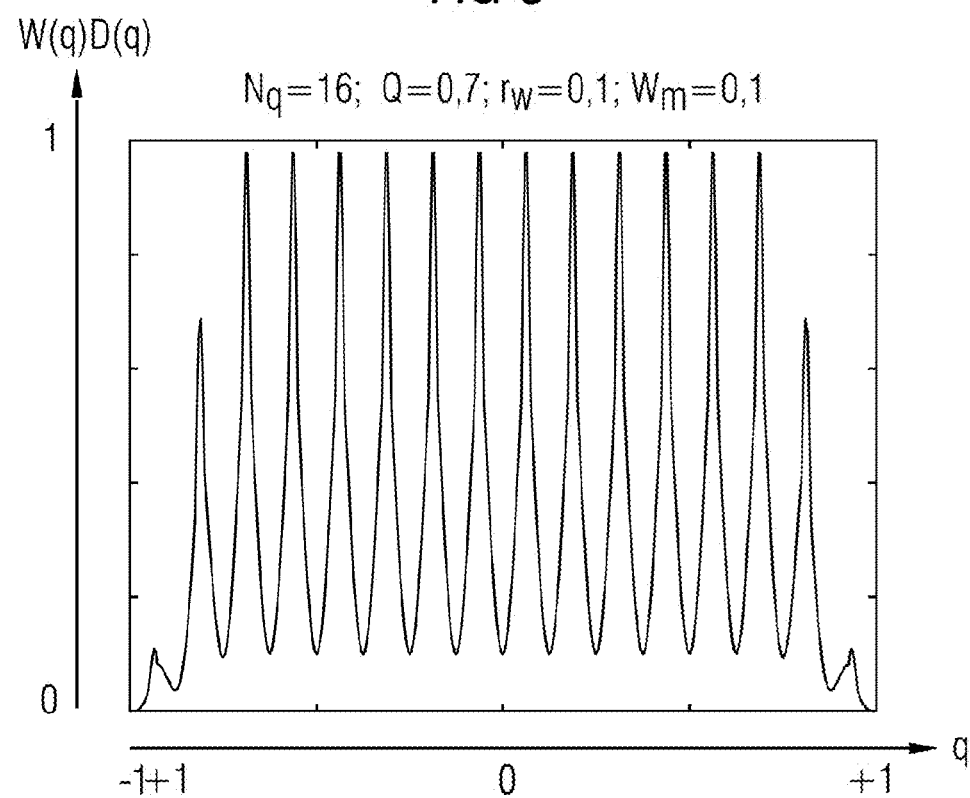
FIG. 8: shows the overlaying of the first weight function from FIG. 5 with a second weight function with narrower peaks.

According to an embodiment of the invention the first and second weighting functions can be overlaid in the form of the product formation W(q)*D(q), so that a comb-type value profile of the weights with a weight reduction at the edges results, as shown in FIG. 7. A further profile of an overall weighting W(q)*D(q), which produces spatially more precise image data, is shown by way of example in FIG. 8 based on the identical first weighting function and a second weighting function with narrower peaks, corresponding to the modified parameter rw=0.1.

Figure 9:
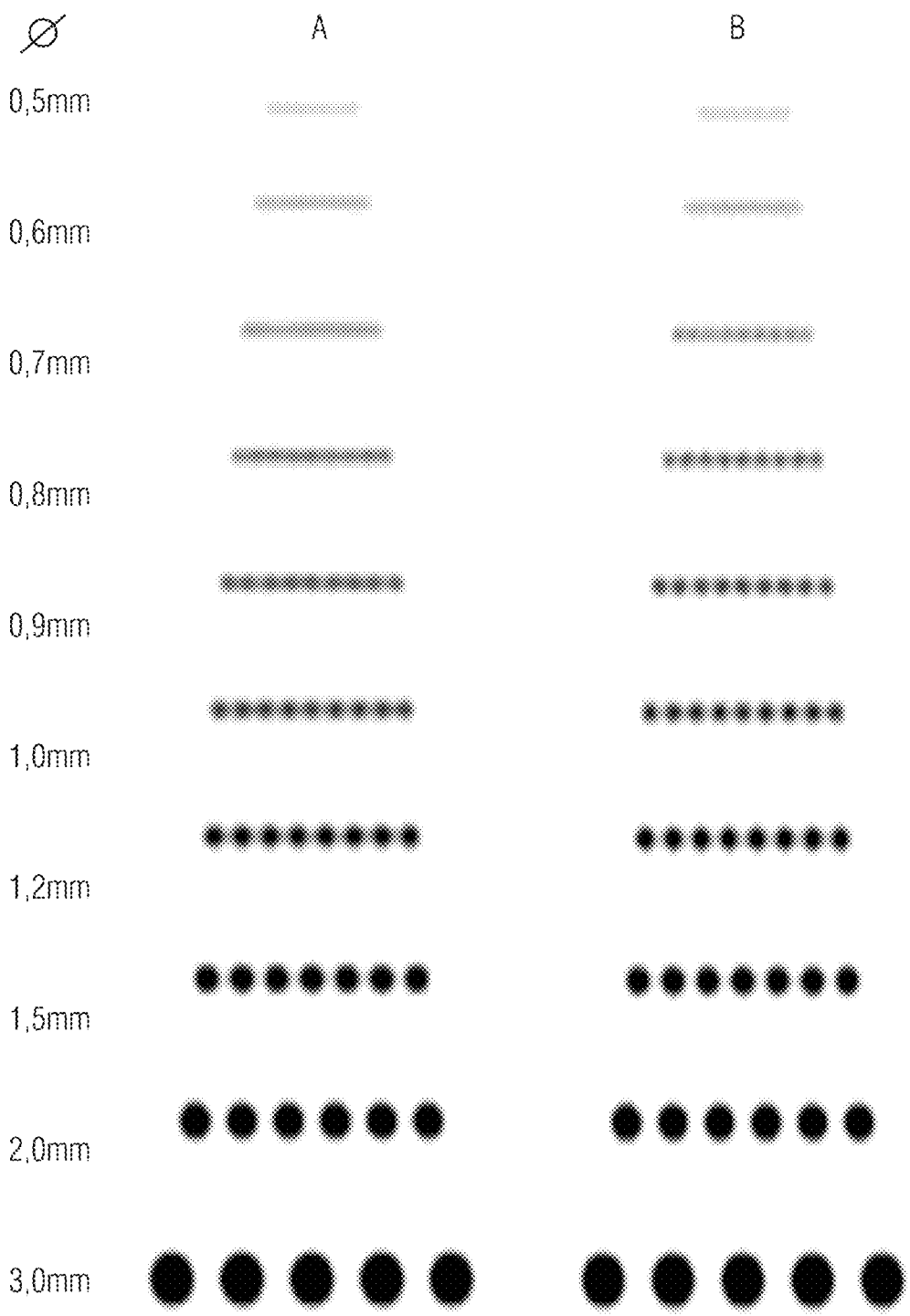
FIG. 9: shows the contrast between a reconstruction result according to the prior art and a reconstruction result according to an embodiment of the invention for a phantom with a number of cylinder structures of different diameters.

Finally FIG. 9 shows the contrast between a reconstruction result with a WFBP method, in which only the first weighting function is used,—left column A—and a reconstruction result with a WFBP method, in which the first weighting function is also overlaid with a comb weighting according to the second weighting function,—right column B. The diagram shows the scanning of a phantom with a number of cylinder structures of different diameters between 0.5 mm and 3.0 mm. It can be seen clearly from the contrasted reconstruction results that the spatial resolution and detailed display are much better with an inventive reconstruction.

Generally therefore an embodiment of the invention describes a method, a computation unit and/or a CT system for reconstructing CT image data, which includes a plurality of image voxels, by way of weighted filtered backprojection, wherein to weight the projection data during the filtered backprojection a weight function is used, which weights the projection data of central beams, which strike a detector row close to the edge of the row, less and the projection data of central beams, which strike a detector row more centrally, more.

Although the invention has been illustrated and described in greater detail by way of the preferred exemplary embodiment, the invention is not restricted by the disclosed examples and other variations can be derived therefrom by the person skilled in the art without departing from the scope of protection of the invention.

What is claimed is:

1. A method for reconstructing CT image data, including a plurality of image voxels, by way of weighted filtered back-projection (WFPB), the method comprising:
   receiving detector data, from at least one multi-row detector rotating about an examination object, detector rows of the at least one multi-row detector extending in a direction perpendicular to a system axis of a CT system;
   calculating convolved projection data from the detector data of adjacent beams, wherein one projection data item of a central beam through the image voxel for each predefined projection angle corresponds to each respective image voxel and wherein a detector row coordinate relative to the detector is allocated to each respective projection data item, which corresponds to a position of the central beam on the detector; and
   weighting the respective projection data as a function of the detector row coordinate allocated to each respective projection data item, wherein a weight function is used to weight the respective projection data during the filtered back-projection, weighting the projection data of central beams striking a detector row close to the edge of the row relatively less, and weighting the projection data of central beams striking a detector row more centrally relatively more; and
   reconstructing the CT image data via the WFPB, based upon respective weighted projection data.

2. The method of claim 1, wherein the weighting of the projection data by the weight function, when considered from row to row, weights projection data with detector row coordinates close to the detector edge generally relatively less and projection data with detector row coordinates in the center of the detector relatively more.

3. The method of claim 2, wherein rebinning is performed before the WFBP reconstruction.

4. The method of claim 1, wherein rebinning is performed before the WFBP reconstruction.

5. The method of claim 1, wherein the weighting for the WFBP reconstruction of each projection is performed independently of other projections from further half rotations of the detector.

6. The method of claim 1, wherein the following formula for backprojection is used to reconstruct the image voxels ($V_{x,y,z}$) according to the WFBP method:

$$V_{x,y,z} = \sum_\theta \frac{1}{\sum_k \tilde{W}(q)} \sum_k \tilde{W}(q) \cdot P_{conv}(p, q, \theta + k\pi),$$

wherein:
   $V_{x,y,z}$ corresponds to the value of the reconstructed voxel at the Cartesian coordinates x, y and z,
   $P_{conv}(p, q, \theta+k\pi)$ corresponds to the rebinned and convolved projection data,
   θ corresponds to the parallel projection angle between 0 and 180°,
   k corresponds to a whole number, which represents the number of half rotations of the detector during scanning,
   q corresponds to the detector row coordinate of the central beam of the voxel $V_{x,y,z}$ projected onto the detector at point x, y, z in the system axis direction with values between −1 and +1 standardized over the detector width,
   $\tilde{W}(q)$ corresponds to the detector row coordinate-dependent weighting function in the WFBP reconstruction.

7. The method of claim 1, wherein to weight the convolved projection data during the filtered back-projection, a weight function is used which is a product of a first weighting function and a second weighting function, wherein:
   the first weight function weights projection data of detector rows located relatively close to the edge in the system axis direction in the detector increasingly relatively less toward the edge than projection data of inner detector rows, and the second weight function has a value profile that alternates in a multiple manner over the detector rows in the system axis direction.

8. The method of claim 7, wherein the alternating value profile of the second weight function has a maximum, in each instance, in the center of the detector rows.

9. The method of claim 8, wherein the maximum is a plateau.

10. The method of claim 7, wherein the alternating value profile of the second weight function has a minimum, in each instance, between the detector rows.

11. The method of claim 7, wherein the overlaying of the weight function is calculated according to the formula $\tilde{W}(q)=W(q) \cdot D(q)$, where the following applies:
   $\tilde{W}(q)$=new weight function,
   $W(q)$=first weight function,
   $D(q)$=second weight function,
   q=coordinate of the detector row in the system axis direction.

12. The method of claim 7, wherein the first weight function ($W(q)$) has a value profile, for which the following applies:

$$W(q) = 1 \text{ for } |q| < Q,$$

$$W(q) = \cos^2\left(\frac{|q|-Q}{Q-1} \cdot \frac{\pi}{2}\right) \text{ for } Q \leq |q| < 1,$$

$W(q)=0$ for all other values of q,
where q is a coordinate of the detector row in the system axis direction and Q is a constant value between 0 and 1, which determines the plateau width of the weight function.

13. The method of claim 12, wherein the second weight function ($D(q)$) has a value profile, for which the following applies:

$$D(q) = \begin{cases} \frac{1+W_m}{2} + \frac{1-W_m}{2}\cos\left(\frac{r}{r_w}\frac{\pi}{2}\right), & \text{for } r \leq r_w \\ \frac{1+W_m}{2} + \frac{1-W_m}{2}\cos\left(\frac{r-r_w}{1-2r_w}\pi + \frac{\pi}{2}\right), & \text{for } r_w < r \leq 1-r_w \\ \frac{1+W_m}{2} + \frac{1-W_m}{2}\cos\left(\frac{r-(1-r_w)}{r_w}\frac{\pi}{2} + \frac{3\pi}{2}\right), & \text{for } r \geq 1-r_w \end{cases}$$

with:

$$r = \frac{q+1}{2}N_q - 0.5 - \left[\frac{q+1}{2}N_q - 0.5\right]$$

where:
   $N_q$ corresponds to the number of detector rows in the detector used,
   the parameter $W_m$ can have values between 0 and 1, corresponding to the minimum values for $D(q)$, and
   the parameter $r_w$ for defining the peak width includes values between 0 and 0.5.

14. The method of claim 7, wherein the second weight function (D(q)) has a value profile, for which the following applies:

$$D(q) = \begin{cases} \frac{1+W_m}{2} + \frac{1-W_m}{2}\cos\left(\frac{r}{r_w}\frac{\pi}{2}\right), & \text{for } r \leq r_w \\ \frac{1+W_m}{2} + \frac{1-W_m}{2}\cos\left(\frac{r-r_w}{1-2r_w}\pi + \frac{\pi}{2}\right), & \text{for } r_w < r \leq 1-r_w \\ \frac{1+W_m}{2} + \frac{1-W_m}{2}\cos\left(\frac{r-(1-r_w)}{r_w}\frac{\pi}{2} + \frac{3\pi}{2}\right), & \text{for } r \geq 1-r_w \end{cases}$$

with:

$$r = \frac{q+1}{2}N_q - 0.5 - \left[\frac{q+1}{2}N_q - 0.5\right]$$

where:
$N_q$ corresponds to the number of detector rows in the detector used,
the parameter $W_m$ can have values between 0 and 1, corresponding to the minimum values for D(q), and
the parameter $r_w$ for defining the peak width includes values between 0 and 0.5.

15. The method of claim 7, wherein the following formula is used to reconstruct the voxels ($V_{x,y,z}$) according to the WFBP method for backprojection:

$$V_{x,y,z} = \sum_\theta \frac{1}{\sum_k W(q)\cdot D(q)} \sum_k W(q)\cdot D(q)\cdot P_{conv}(p, q, \theta + k\pi),$$

where:
$V_{x,y,z}$ corresponds to the value of the reconstructed voxel at the Cartesian coordinates x, y and z,
$P_{conv}(p, q, \theta+k\pi)$ corresponds to the rebinned and convolved projection data,
θ corresponds to the parallel projection angle between 0 and 180°,
k corresponds to a whole number, which represents the number of half rotations of the detector during scanning,
q corresponds to the detector row coordinate of the voxel $V_{x,y,z}$ projected onto the detector at point x, y, z in the system axis direction with values between −1 and +1 standardized over the detector width,
W(q) corresponds to the first weighting function and
D(q) corresponds to the second weighting function.

16. The method of claim 7, wherein the weighting for the WFBP reconstruction for each projection is performed independently of other projections from further half rotations of the detector.

17. The method of claim 1, wherein the detector data originates from a CT spiral scan.

18. The method of claim 17, wherein an advance speed is used, which produces overlapping scan regions.

19. The method of claim 1, wherein the detector data originates from a CT circular scan.

20. The method of claim 19, wherein the CT circular scan is performed in such a manner that overlapping scan regions are produced.

21. The method of claim 1, wherein the method is applied in an iterative reconstruction method.

22. A computation unit for performing a WFBP reconstruction, comprising:
at least one processor;
a memory configured to store a computer program; and
an output unit, wherein the computer program performs the method of claim 1 when executed on the at least one processor.

23. The computation unit of claim 22, wherein at least one manually operable controller is provided, by which at least one parameter can be set before each image calculation, defining the form of at least one weighting function.

24. A CT system comprising the computation unit of claim 23.

25. A method for the iterative reconstruction of CT image data which includes a plurality of image voxels, the method comprising:
performing at least one weighted back-projection of convolved projection data in the iteration;
calculating the convolved projection data from detector data of adjacent beams;
assigning a projection data item of a central beam through the image voxel, for each predefined projection angle, to each respective image voxel; and
allocating a detector row coordinate relative to the detector, which corresponds to the position of the central beam on the detector, to each projection data item, wherein to weight the projection data, a weight function is used, the weight function weighting the projection data of central beams which strike a detector row relatively close to the edge of the row relatively less, and weighting the projection data of central beams which strike a detector row more relatively centrally relatively more; and
reconstructing the CT image data based upon respective weighted projection data.

26. The method of claim 25, wherein the weighting of the projection data by the weight function, when considered from row to row, weights projection data with detector row coordinates relatively close to the detector edge generally relatively less and projection data with detector row coordinates relatively in the center of the detector relatively more.

27. The method of claim 25, wherein to weight the convolved projection data, a weight function is used which is a product of a first weighting function and a second weighting function, and wherein:
the first weight function weights projection data of detector rows located relatively close to the edge in the system axis direction in the detector increasingly less toward the edge than projection data of inner detector rows, and
the second weight function has a value profile that alternates in a multiple manner over the detector rows in the system axis direction.

28. The method of claim 27, wherein the alternating value profile of the second weight function includes a maximum in each instance in the center of the detector rows.

29. The method of claim 27, wherein the alternating value profile of the second weight function includes larger values in the center of the detector rows than toward the edge of the detector rows.

* * * * *